United States Patent [19]

Robinson et al.

[11] Patent Number: 6,057,462
[45] Date of Patent: May 2, 2000

[54] ISOLATION AND PURIFICATION OF STEROLS FROM NEUTRALS FRACTION OF TALL OIL PITCH BY SINGLE DECANTATION CRYSTALLIZATION

[75] Inventors: Philip L. Robinson, Isle of Palms; Thomas J. Cuff; Julian E. Parker, III, both of Charleston, all of S.C.

[73] Assignee: Westvaco Corporation, New York, N.Y.

[21] Appl. No.: 09/187,448

[22] Filed: Nov. 6, 1998

[51] Int. Cl.[7] .......................................................... C07J 9/00
[52] U.S. Cl. ................................................................ 552/545
[58] Field of Search .............................. 260/397; 552/545

[56] References Cited

U.S. PATENT DOCUMENTS 2,573,891  11/1951  Christenson ............................. 260/397
3,840,570  10/1974  Julian ...................................... 260/397

*Primary Examiner*—Jose' G. Dees
*Assistant Examiner*—Alton Pryor
*Attorney, Agent, or Firm*—Terry B. McDaniel; Daniel B. Reece, IV; Richard L. Schmalz

[57] ABSTRACT

Sterols from the solvent-extracted or distilled neutrals of saponified tall oil pitch are disclosed to be isolated and purified by a process of a liquid-liquid extraction where the hydrocarbon extraction stream is washed with an aqueous methanol solution to remove methanol-soluble impurities by adding the methanol and water, sequentially or as a blend. The resulting hydrocarbon/neutrals/methanol/water solution separates into an upper organic phase and a lower methanol/water phase, which lower phase is removed. The remaining organic phase is allowed to cool to from about 20–30° C., with agitation, to facilitate crystallization of sterols, which crystals are recovered by filtering.

8 Claims, 2 Drawing Sheets

ISOLATION AND PURIFICATION OF STEROLS FROM NEUTRALS FRACTION OF TALL OIL PITCH BY SINGLE DECANTATION CRYSTALLIZATION

BACKGROUND OF THE INVENTION

1. Field of the Invention

The present invention is related to methods of isolating and purifying the valuable constituents from Crude Tall Oil (CTO) recovered from the black liquor residue of wood pulping processes, primarily used in making paper. More particularly, the present invention is related to methods of extraction of valuable constituents from the neutrals fraction of CTO. Most particularly, the present invention is related to methods of isolation and purification of extracted or distilled constituents of the neutrals fraction of CTO which, upon said purification and subsequent modification, are useful as a dietary supplement in foods to reduce cholesterol levels in humans.

2. Description of Related Art (Including Information Disclosed Under 37 CFR 1.97 and 37 CFR 1.98)

It has long been appreciated that the black liquor residue from wood pulping contains valuable chemicals, which make up the CTO, with various industrial applications. The black liquor contains the soaps of rosin and fatty acids, as well as sodium lignate and the spent cooking chemicals for reuse. The CTO is recovered by partially evaporating the black liquor, for concentration purposes, and then skimming off the tall oil soaps that float to the top of a skimming tank. The soap skimmings are converted to CTO by reaction with sulfuric acid and then separated from the simultaneously-formed spent acid by batch cooking, continuous centrifuging, or continuous decanting. The CTO is normally divided into various fractions by distillation which first extracts the pitch (or bottoms). The depitched CTO is then separated into fractions of heads, tall oil rosin (TOR), tall oil fatty acids (TOFA), and distilled tall oil (DTO). A major ingredient of the neutral fraction of CTO, concentrated in the pitch fraction thereof, is a class of compounds known as sterols, including β-sitosterol. It is known, however, that a common place to obtain these sterols is via solvent extraction of tall oil soap, which is done commercially in Scandinavia.

Recently, U.S. Pat. No. 5,502,045 disclosed the use (by ingestion) of a sitostanol fatty acid ester for reducing serum cholesterol level. The patent's assignee, Raisio, a Finnish manufacturer of foodstuffs, grain, and specially chemicals, has developed a cholesterol-reducing margarine called Benecol®. The active ingredient (in cholesterol reduction) in Benecol® is the claimed fat-soluble stanol ester which prevents cholesterol from being absorbed into the human digestive system. The stanol ester is produced from plant-derived sterols (phytosterols) via hydrogenation and trans esterification reactions. Cholesterol reductions (LDL and HDL) of 10–15% are common for individuals with diets containing Benecol®.

Therefore, the value of recovering plant-derived sterols has become enhanced and the particular problems associated with recovering sistosterol from tall oil pitch have become worthy of investigation. A viable commercial process must achieve a high percent recovery of neutrals and/or sterols (greater than 70% recovery is preferable) and achieve high final sterol purity (higher than 95% is desirable). Past attempts to extract neutrals/sterols from one or more fractions of CTO are reported in the following patents:

| Patent No. | Inventor | Title | Issue Date |
| --- | --- | --- | --- |
| U.S. Pat. No. 2,499,430 | Vogel et al. | "Obtaining Sterols of High Purity" | Mar 7, 1950 |
| U.S. Pat. No. 2,530,809 | Christenson et al. | "Fractionation of Tall Oil" | Nov 21, 1950 |
| U.S. Pat. No. 2,530,810 | Christensen, et al. | "Separation of Unsaponifiable Matter from Tall Oil Residue" | Nov 21, 1950 |
| U.S. Pat. No. 2,547,208 | Hasselstrom et al. | "Method for the Refining of Tall Oil Residue" | Apr 3, 1951 |
| U.S. Pat. No. 2,715,638 | Albrecht et al. | "Production of Sterols from Tall Oil Pitch" | Aug 16, 1955 |
| U.S. Pat. No. 2,835,682 | Steiner et al. | "Sterol Recovery Process" | May 20, 1958 |
| U.S. Pat. No. 2,866,781 | Chase et al. | "Separating Non-acids from Soap Stocks" | Dec 30, 1958 |
| U.S. Pat. No. 2,866,797 | Berry et al. | "Improved Process of Isolating Sterols" | Dec 30, 1958 |
| U.S. Pat. No. 3,840,570 | Julian et al. | "Process for Preparing Sterols from Tall Oil Pitch" | Oct 8, 1974 |
| U.S. Pat. No. 3,879,431 | Clark et al. | "Purification of Sterols by Distillation" | Apr 22, 1975 |
| U.S. Pat. No. 3,965,085 | Holmbom et al. | "Method for Refining of Soaps Using Solvent Extraction" | Jun 22, 1976 |
| U.S. Pat. No. 4,044,031 | Johansson et al. | "Process for the Separation of Sterols" | Aug 23, 1977 |
| U.S. Pat. No. 4,124,607 | Beaton et al. | "Preparation of Sterol Substrates for Bioconversion" | Nov 7, 1978 |
| U.S. Pat. No. 4,420,427 | Hamunen | "Process for the Separation of Sterols or Mixtures of Sterols" | Dec 13, 1983 |
| U.S. Pat. No. 4,422,966 | Amer | "Separation of Neutrals from Tall Oil Soaps" | Dec 27, 1983 |
| U.S. Pat. No. 4,496,478 | Kulkarni et al. | "Process for Separating Unsaponifiables from Fatty and Rosin Acids" | Jan 29, 1985 |
| U.S. Pat. No. 4,524,024 | Hughes | "Processes of Recovering Fatty Acids and Sterols from Tall Oil Pitch" | Jun 18, 1985 |
| U.S. Pat. No. 4,849,112 | Barder et al. | "Adsorption Separation of Sterols from Tall Oil Pitch with Carbon Adsorbent" | Jul 18, 1989 |
| U.S. Pat. No. 4,935,168 | Sjöberg et al. | "Process for the Preparation of Alcohols" | Jun 19, 1990 |
| U.S. Pat. No. 5,097,012 | Thies et al. | "Solvent Extraction of Fatty Acid Stream with Liquid Water and Elevated Temperatures and Pressures" | Mar 17, 1992 |

These approaches have failed to provide both a high percent recovery of neutrals and/or sterols and a high final sterol purity. Recently, it was discovered that sterols could be isolated from the solvent extraction neutrals mixture from a tall oil pitch fraction using a direct precipitation process (described in commonly-owned application Ser. No. 09/115, 003 filed on Jul. 1, 1998). Briefly, in the direct precipitation process, a small amount of methanol is added to the partially concentrated neutrals, the mixture is allowed to cool to 20–30° C., and water is added to precipitate the sterols, again at 20–30° C. However, this often results in precipitating very small crystals, which can present difficulties as the small crystals are filtered during the sterol isolation step. It is anticipated that generation of larger crystals not only would improve sterol filterability, but improved sterol yields and purity as well.

Therefore, it is an object of this invention to provide a method for recovering the solvent-extracted or distilled neutral fraction of saponified tall oil pitch and isolating a high percentage of the sterol component thereof, by treating the neutral fraction to isolate therefrom sterol crystals of enhanced size to result in improved sterol yields and purity.

SUMMARY OF THE INVENTION

The above-stated objects of the invention are achieved by isolating the sterol component of the neutrals fraction of saponified tall oil pitch. The isolation may be accomplished by a liquid-liquid extraction from the neutrals where a blend of an alcohol solvent (preferably methanol) and water is added to the hydrocarbon extraction stream at elevated temperatures, preferably a range of about 60–70° C. The mixture separates into a lower methanol-water phase and an upper organic phase. (Alternatively, this addition may be accomplished step-wise by first adding alcohol to the hydrocarbon/neutrals stream and then adding water. The subsequent phase separation similarly occurs.) The alcohol-soluble impurities remain in the aqueous-alcohol solution phase, which is decanted. The remaining organic phase is allowed to cool to about 20–35° C. allowing sterol crystal formation. Finally, the sterol crystals are recovered by solid-liquid separation.

BRIEF DESCRIPTION OF THE DRAWING(S)

DESCRIPTION OF THE PREFERRED EMBODIMENT(S)

The invention single decantation crystallization process of recovering sterols from a solution of extracted, or distilled, tall oil pitch neutrals in a hydrocarbon solvent, preferably heptane, is accomplished either (1) by adding an alcohol (preferably methanol) to such solution, followed by an addition of water to the hydrocabon/neutrals/alcohol, or (2) by adding a blend of the alcohol solvent and water to the hydrocarbon/neutrals solution. In either case, such additions are made at elevated temperatures (from about 60° to about 70° C.). The resultant hydrocarbon/neutrals/alcohol/water mixture is allowed to settle and to separate into two phases.

The bottom phase (water with some methanol) is withdrawn (decanted) from the reactor, and the hot top (organic) phase is transferred to a crystallization vessel, where the mixture is slowly cooled to a temperature of about 20–35° C., with stirring, to promote crystallization. The crystals are isolated by filtering and washing with two parts of fresh heptane.

Figure 1:
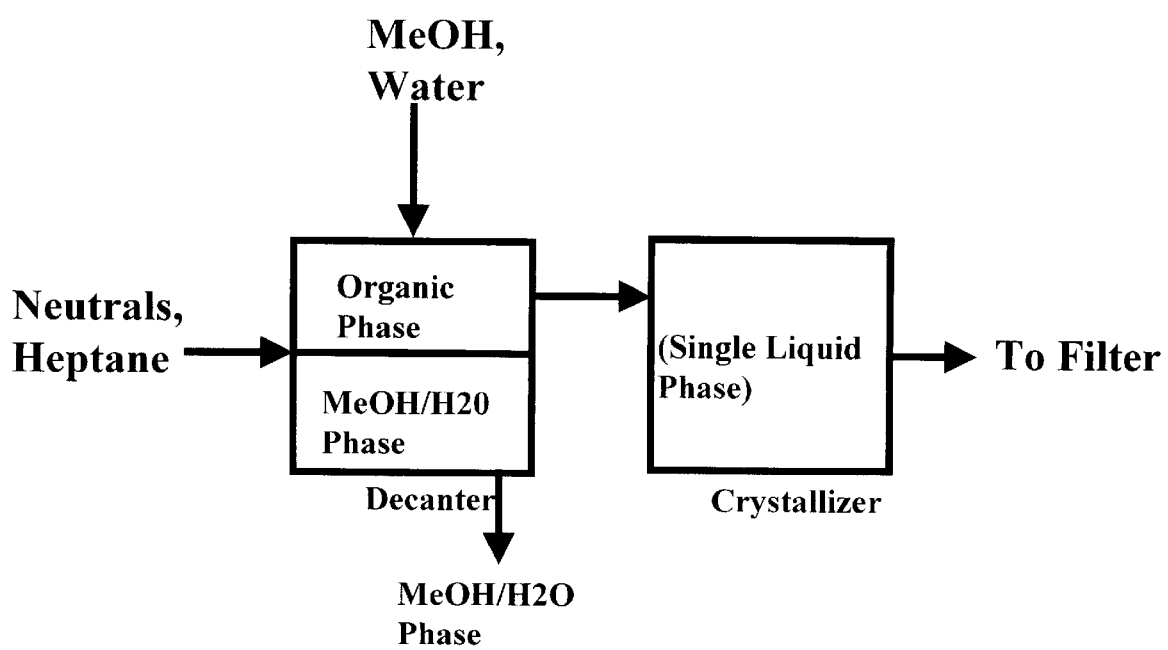
FIG. 1 represents a flow diagram of the claimed invention single decantation-crystallization process of the isolation and purification of sterols from solvent-extracted neutrals of tall oil pitch in a hydrocarbon stream by adding a blend of an alcohol and water.
Figure 2:
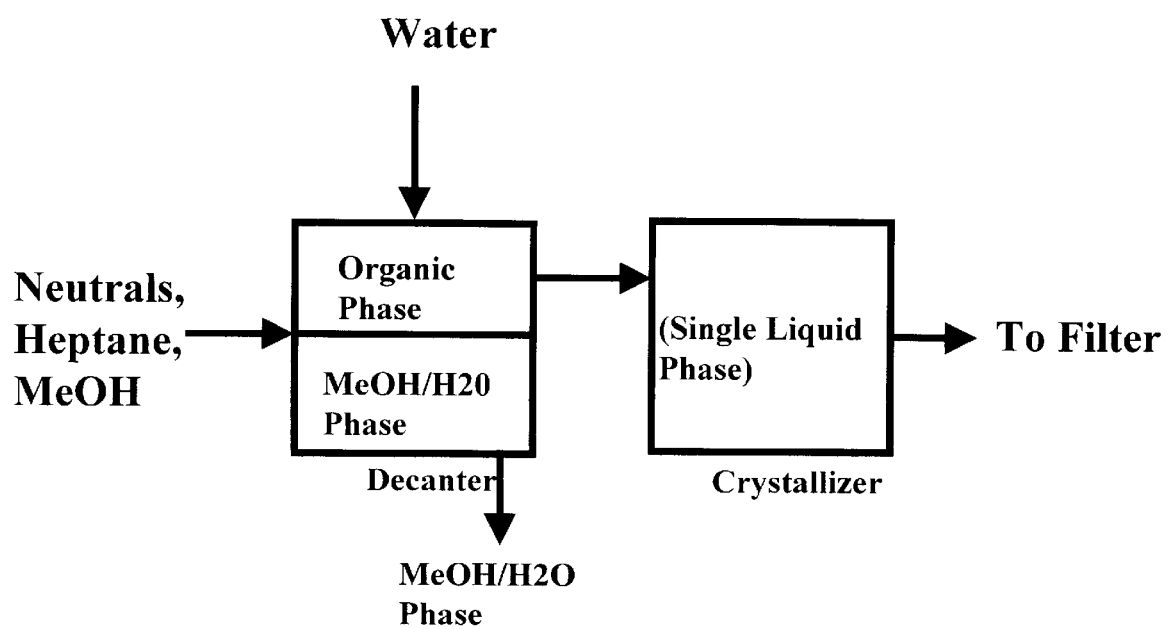
FIG. 2 represents a flow diagram of the claimed process of the invention single decantation-crystallization isolation and purification of sterols from solvent-extracted neutrals of tall oil pitch in a hydrocarbon stream by pre-blending said stream with alcohol prior to water addition.

Following the process steps recited above, data were collected for 22 examples, reported below. This data was generated for random combinations of high and low values for six variables, which included the heptane content, wash methanol content, wash water content, final crystallization temperature, crystallization time, and agitation rate. The procedure for the examples involved the invention embodiment wherein the alcohol was pre-mixed with the hydrocarbon/neutrals stream prior to water addition (as shown in FIG. 2). The key variables and ranges are listed in Table 1. The results examined included the mass yield, sterol yield, sterol purity and wax alcohol content.

TABLE I

Variables and Ranges for the Quarter Fractional, Factorial DOE for the SDC Process

| Factor[a] | Low | High |
| --- | --- | --- |
| Heptane Content (parts) | 2.0 | 5.0 |
| Wash Methanol Content (parts) | 0.55 | 0.95 |
| Wash Water (parts) | 0.5 | 1.5 |
| Final Crystallization Temperature (° C.) | 20 | 30 |
| Crystallization Time (hours) | 1.0 | 4.0 |
| Agitation Rate[b] (rpm) | 20 | 100 |

[a]Parts refers to the relative weight ratio of the variable to the amount of dry neutrals used in the experiment.
[b]Agitation rate refers to the rate of agitation of the organic phase during crystallization.

The results from each condition of the experimental design are given in Table II.

TABLE II

Results of Quarter Fractional, Factorial Experimental Design using the SDC Process

| Example | Heptane (parts) | Wash Methanol (parts) | Wash. Water (parts) | Final Temp. ° C. | Crystal. Time (hours) | Agitation Rate (RPM) | Mass Yield (%) | Sterol Yield (%) | Purity (%) | Wax Alcohol (%) |
| --- | --- | --- | --- | --- | --- | --- | --- | --- | --- | --- |
| 1 | 3.5 | 0.75 | 1.0 | 25 | 2.5 | 60 | 62.5 | 58.3 | 93.2 | 0.0 |
| 2 | 3.5 | 0.75 | 1.0 | 25 | 2.5 | 60 | 64.7 | 60.7 | 93.8 | 0.0 |
| 3 | 2.0 | 0.55 | 1.5 | 20 | 4.0 | 100 | 73.1 | 59.1 | 80.8 | 7.0 |
| 4 | 5.0 | 0.55 | 0.5 | 30 | 4.0 | 100 | 54.8 | 51.0 | 93.0 | 0.0 |
| 5 | 2.0 | 0.95 | 0.5 | 30 | 4.0 | 20 | 61.8 | 58.2 | 94.2 | 0.0 |
| 6 | 2.0 | 0.95 | 1.5 | 20 | 1.0 | 20 | 78.2 | 61.7 | 78.9 | 9.0 |

TABLE II-continued

Results of Quarter Fractional, Factorial Experimental Design using the SDC Process

| Example | Heptane (parts) | Wash Methanol (parts) | Wash. Water (parts) | Final Temp. °C. | Crystal. Time (hours) | Agitation Rate (RPM) | Mass Yield (%) | Sterol Yield (%) | Purity (%) | Wax Alcohol (%) |
|---|---|---|---|---|---|---|---|---|---|---|
| 7 | 2.0 | 0.55 | 1.5 | 30 | 4.0 | 20 | 73.1 | 60.5 | 82.7 | 7.5 |
| 8 | 2.0 | 0.95 | 1.5 | 30 | 1.0 | 100 | 62.2 | 59.2 | 95.2 | 0.0 |
| 9 | 5.0 | 0.55 | 0.5 | 20 | 4.0 | 20 | 72.8 | 58.2 | 80.0 | 8.2 |
| 10 | 5.0 | 0.95 | 0.5 | 20 | 1.0 | 100 | 67.4 | 61.8 | 91.7 | 0.0 |
| 11 | 5.0 | 0.55 | 1.5 | 20 | 1.0 | 100 | 77.4 | 64.3 | 83.1 | 6.5 |
| 12 | 5.0 | 0.55 | 1.5 | 30 | 1.0 | 20 | 57.3 | 57.2 | 99.8 | 0.0 |
| 13 | 2.0 | 0.55 | 0.5 | 30 | 1.0 | 100 | 69.9 | 65.9 | 94.3 | 0.0 |
| 14 | 5.0 | 0.95 | 1.5 | 20 | 4.0 | 20 | 76.8 | 65.0 | 84.7 | 3.8 |
| 15 | 5.0 | 0.95 | 0.5 | 30 | 1.0 | 20 | 53.1 | 48.9 | 92.0 | 0.0 |
| 16 | 3.5 | 0.75 | 1.0 | 25 | 2.5 | 60 | 68.0 | 63.5 | 93.4 | 0.0 |
| 17 | 3.5 | 0.75 | 1.0 | 25 | 2.5 | 60 | 67.8 | 63.2 | 93.2 | 0.0 |
| 18 | 5.0 | 0.95 | 1.5 | 30 | 4.0 | 100 | 60.8 | 55.2 | 90.8 | 0.0 |
| 19 | 3.5 | 0.75 | 1.0 | 25 | 2.5 | 60 | 66.3 | 59.1 | 89.2 | 2.1 |
| 20 | 2.0 | 0.55 | 0.5 | 20 | 1.0 | 20 | 80.5 | 64.6 | 80.2 | 5.5 |
| 21 | 3.5 | 0.75 | 1.0 | 25 | 2.5 | 60 | 72.4 | 63.7 | 88.0 | 3.5 |
| 22 | 2.0 | 0.95 | 0.5 | 20 | 4.0 | 100 | 70.1 | 64.5 | 92.0 | 0.0 |
| Center point Mean and Standard Deviation | | | | | | | 67.0 ± 3.1 | 61.4 ± 2.2 | 91.9 ± 2.3 | 0.93 ± 1.4 |
| Mean and Standard Deviation for all Runs | | | | | | | 67.8 ± 7.6 | 60.2 ± 4.4 | 89.3 ± 6.0 | 2.4 ± 3.3 |

Mass yields ranged from 53.1–80.5%, sterol yields ranged from 48.9–65.9%, sterol purities ranged from 78.9–99.8%, and wax alcohol content ranged from 0–9.0%. The best conditions, run 13, gave a 65.9% sterol yield with 94.3% purity and no wax alcohols.

Statistical analyses of the data using StatGraphics software show that final temperature and heptane content were statistically significant in affecting mass yield and sterol yield. Various combination effects were also significant for yield. Final temperature was the only significant variable affecting sterol purity, and it was the most significant variable for wax alcohol content, with methanol only slightly significant. As expected, lower heptane loadings and temperatures gave higher yields. On the other hand, higher temperatures favored better purities and lower wax alcohol contaminations. Lower methanol loadings also reduce wax alcohols.

The mean and standard deviation for the six center point experiments in the quarter fractional factorial experiment with the SDC process were 67.0±3.1% for mass yield, 61.4±2.2% for sterol yield, 91.9±2.3% for sterol purity, and 0.93±1.4 for wax alcohol content.

The R-squared values show that the model as fitted explains 92.2% of the variation in mass yield, 89.8% of the variation in sterol yield, 82.8% of the variation in sterol purity, and 81.0% of the variation in wax alcohol content.

The subject matter of the invention is:
(1) A method for the isolation of sterols from sulfate pulping process tall oil pitch comprising the steps of:
  (a) saponifying the tall oil pitch;
  (b) separating the neutral fraction from the saponified tall oil pitch;
  (c) blending a hydrocarbon solution of the neutrals with an alcohol solvent at a temperature greater than the crystallization temperature of sterol to produce a hydrocarbon/neutrals/alcohol solution;
  (d) adding water of a temperature higher than that of the hydrocarbon/neutrals/alcohol solution to separate into an upper organic phase and a lower alcohol/water phase;
  (e) removing the lower alcohol/water phase;
  (f) the remaining upper organic phase is allowed to cool to a final temperature from about 20° C. to about 30° C. to produce sterol crystals; and
  (g) the sterol crystals are recovered from the cooled solution;
(2) The method of (1) wherein the extraction neutrals of tall oil pitch are derived by a process selected from the group consisting of solvent extraction and distillation;
(3) The method of (1) wherein the hydrocarbon solvent is selected from the group consisting of straight- and branched-chain hydrocarbons with from 5 to 10 carbons;
(4) The method of (3) wherein the hydrocarbon solvent is selected from the group consisting of pentane, hexane, heptane, iso-octane, and mixtures thereof;
(5) The method of (1) wherein the alcohol solvent is an aliphatic alcohol;
(6) The method of (5) wherein the alcohol solvent is selected from the group of aliphatic alcohols consisting of methanol, ethanol, butanol, iso-propanol, and mixtures thereof;
(7) The method of (1) wherein the temperature in step (a) is greater than 60° C.;
(8) The method of (1) wherein the temperature in step (a) is greater than 70° C.;
(9) The method of (1) further comprising washing the recovered sterol crystals with a hydrocarbon solvent to obtain a high yield of sterols of high purity; and
(10) The method of (9) wherein the sterol yield is at least 60% and the sterol purity is at least 90%.

Modifications to this invention will occur to those skilled in the art. Therefore, it is to be understood that this invention is not necessarily limited to the particular embodiments disclosed; rather, it is intended to cover all modifications which are within the true spirit and scope of this invention, as disclosed and claimed herein.

What is claimed is:

1. A method for the isolation of sterols from sulfate pulping process tall oil pitch comprising the steps of:
  (a) saponifying the tall oil pitch;
  (b) extracting the neutral fraction from the saponified tall oil pitch;
  (c) blending a hydrocarbon solution of the neutrals with an alcohol solvent at a temperature greater than the crystallization temperature of sterol to produce a hydrocarbon/neutrals/alcohol solution;

(d) adding water of a temperature higher than that of the hydrocarbon/neutrals/alcohol solution to separate into an upper organic phase and a lower alcohol/water phase;

(e) removing the lower alcohol/water phase;

(f) allowing the remaining upper organic phase to cool to a final temperature from about 20° C. to about 30° C. to produce sterol crystals;

(g) recovering the sterol crystals from the cooled solution; and (h) washing the recovered sterol crystals with a hydrocarbon solvent to obtain a sterol yield of at least 60% and a sterol purity of at least 90%.

2. The method of claim 1 wherein the extraction neutrals of tall oil pitch are derived by a process selected from the group consisting of solvent extraction and distillation.

3. The method of claim 1 wherein the hydrocarbon solvent is selected from the group consisting of straight- and branched-chain hydrocarbons with from 5 to 10 carbons.

4. The method of claim 3 wherein the hydrocarbon solvent is selected from the group consisting of pentane, hexane, heptane, iso-octane, and mixtures thereof.

5. The method of claim 1 wherein the alcohol solvent is an aliphatic alcohol.

6. The method of claim 5 wherein the alcohol solvent is selected from the group of aliphatic alcohols consisting of methanol, ethanol, butanol, iso-propanol, and mixtures thereof.

7. The method of claim 1 wherein step (a) is conducted at a temperature greater than 60° C.

8. The method of claim 1 wherein step (a) is conducted at a temperature greater than 70° C.

* * * * *